United States Patent [19]

Szita et al.

[11] 4,356,304

[45] Oct. 26, 1982

[54] SYNTHESIS OF OXYALKYLATED POLYAMINO-1,3,5-TRIAZINES

[75] Inventors: Jeno G. Szita, Norwalk; Roland R. DiLeone, Rowayton, both of Conn.

[73] Assignee: American Cyanamid Company, Stamford, Conn.

[21] Appl. No.: 285,729

[22] Filed: Jul. 22, 1981

Related U.S. Application Data

[63] Continuation-in-part of Ser. No. 211,889, Nov. 10, 1980, abandoned.

[51] Int. Cl.$^3$ .................. C07D 251/18; C07D 251/70
[52] U.S. Cl. .................. 544/196; 544/197; 544/205; 544/206
[58] Field of Search .......... 544/196, 197, 205, 206

[56] References Cited

U.S. PATENT DOCUMENTS

| | | | |
|---|---|---|---|
| 2,594,452 | 4/1952 | Kosmin | 544/196 |
| 3,328,321 | 6/1967 | Wismer et al. | 544/196 X |
| 3,438,986 | 4/1969 | Kaiser et al. | 544/196 |
| 3,573,301 | 3/1971 | Winter | 544/196 |
| 3,679,589 | 7/1972 | Schnegelberger et al. | 544/196 |
| 3,988,337 | 10/1976 | Narayan et al. | 544/196 |
| 4,013,655 | 3/1977 | Merz et al. | 544/196 |

*Primary Examiner*—John M. Ford
*Attorney, Agent, or Firm*—Steven J. Hultquist

[57] ABSTRACT

A process for synthesizing oxyalkylated polyamino-1,3,5-triazines involves reacting a hydroxyalkyl ($C_2$–$C_{12}$) or hydroxyaryl polyamino-1,3,5-triazine with an alkylene oxide at an elevated temperature.

13 Claims, No Drawings

SYNTHESIS OF OXYALKYLATED POLYAMINO-1,3,5-TRIAZINES

CROSS REFERENCE TO RELATED APPLICATION

This application is a continuation-in-part of U.S. Ser. No. 211,889 filed Nov. 10, 1980, now abandoned.

This invention relates generally to a process for preparing oxyalkylated polyamino-1,3,5-triazine compounds. More particularly, the invention comprises reacting a hydroxyalkyl ($C_2$–$C_{12}$) or hydroxyaryl polyamino-1,3,5-triazine with an alkylene oxide at an elevated temperature and in the substantial absence of a solvent.

Early attempts to prepare oxyalkylated polyamino-1,3,5-triazines by directly reacting the triazine compound with an alkylene oxide in the absence of a solvent (such as is disclosed in U.S. Pat. No. 2,381,121) gave very poor yields. Hence, oxyalkylated polyamino-1,3,5-triazines are prepared by oxyalkylating the polyamino-1,3,5-triazine using either a low molecular weight dialkyl sulfoxide or an N,N-dialkyl acid amide as a solvent. U.S. Pat. Nos. 3,399,151 and 3,812,122, respectively, disclose the use of these solvents. However, removal of these high boiling, polar compounds from the oxyalkylated polyamino-1,3,5-triazine is extremely difficult and costly. As a result, the final product, which finds use in the manufacture of rigid, semi-rigid and flexible polyurethane foams, and as a textile auxiliary, paper processing aid and mining frother, is expensive and not of uniformly good quality.

U.S. Pat. No. 2,594,452 discloses the reaction of methylol melamines and epoxides, but in the presence of water as a solvent. By having the water present, the formation of polyalkylene oxides, i.e., polyethylene oxide, is favored over the addition to the methylol melamine. Furthermore, methylol melamines are not useful herein as under the present conditions they would homopolymerize to form a cross-linked intractable system.

U.S. Pat. No. 3,438,986 teaches the use of a reactive solvent, i.e., an oxyalkylated aryl diamine, during the oxyalkylation reaction. This solvent does not have to be later removed but it is nonetheless a solvent.

Furthermore, the solvent based processes of the prior art result in only high molecular weight products whereas the present invention permits the tailor-making of any desired molecular weight and produces a narrow molecular weight range product.

It is accordingly an object of this invention to provide a process for oxyalkylating a polyamino-1,3,5-triazine compound which will avoid the problems encountered in the current processes which employ solvents.

It is a further object of this invention to provide, by such process, oxyalkylated polyamino-1,3,5-triazines in good yield and excellent purity, which are lighter in color than the compounds produced by the previous solvent processes, thereby enhancing the commercial appeal thereof.

These and other objects of the instant invention will become apparent from the ensuing description.

It has been discovered that the above mentioned objects may be accomplished by a process wherein a hydroxyalkyl ($C_2$ or greater) or hydroxyaryl polyamino-1,3,5-triazine is reacted with an alkylene oxide at a temperature from about 80° C. to 200° C. The process is carried out in the substantial absence of any solvent.

Hydroxyalkyl or hydroxyaryl triazine compounds having the formula:

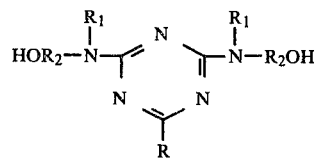

wherein R is hydrogen, alkyl or cycloalkyl with from about 1–12, preferably 1–6, carbon atoms; alkylene with from about 3–20, preferably 3–6, carbon atoms; aryl with from 6–12 carbon atoms; $NH_2$ or $NR_1R_2OH$; $R_1$ is hydrogen or $R_2OH$; and each $R_2$ is independently alkylene with from about 2–12, preferably 2–4, carbon atoms or arylene with from about 6–12 carbon atoms, are typically used in the process of the instant invention.

The hydroxyalkyl or hydroxyaryl triazine starting material may be prepared by any method known to the art, the particular method not constituting a feature of the instant invention.

The alkylene oxides generally used in the process of the present invention include linear, cyclic or aromatic substituted alkylene oxides having about 2–22 carbon atoms as well as any of such alkylene oxides which contain non-interfering substituents. Examples of preferred alkylene oxides include: ethylene oxide, propylene oxide, butylene oxide, isobutylene oxide, n-hexylene oxide, cyclohexene oxide, and styrene oxide. The alkylene oxides may be employed singularly, in alternating sequence, or as mixtures.

The molar ratio of the hydroxyalkyl or hydroxyaryl-polyamino-1,3,5-triazine to alkylene oxide may be varied within wide limits. Generally, the ratio is from about 1:2 to 1:125. Preferably, the ratio is from about 1:4 to 1:40. Most preferably, the ratio is from about 1:4 to 1:10.

The reaction is generally conducted in the presence of an organic or inorganic basic catalyst. Usual catalysts include alkali hydroxides such as potassium hydroxyide and sodium hydroxide, and alkali alkoxides having from 1 to 4 carbon atoms in the alkyl group, such as sodium methoxide, potassium ethoxide and the like. Sufficient catalyst is used to accelerate the rate of the reaction, with generally from about 0.1 to 1.0 moles per kilogram of hydroxyalkyl or hydroxyaryl polyamino-1,3,5-triazine added. Preferably, from 0.2 to 0.5 moles of catalyst per kilogram of hydroxyalkyl or hydroxyaryl polyamino-1,3,5-triazine is used. However, more or less catalyst may be employed if desired.

Generally, the reaction is run at a temperature between about 80° C. and 200° C., with from about 100° C. to 150° C. being preferred. It is understood, however, that the temperature will depend in large part upon the particular reactants and catalyst used as well as the proportions thereof.

The reaction is usually completed over a period of from about 1 to 10 hours, preferably 3 to 7 hours, at atmospheric pressure. Alternatively, the reaction may be conducted under elevated pressure of from about 1 to 10, preferably 2 to 6, atmospheres.

The process, according to the present invention, is further detailed by the following examples, but it is not deemed to be in any way limited thereby. All parts and percentages are by weight unless otherwise indicated.

EXAMPLE 1

This example illustrates one method of preparing a hydroxyalkyl polyamino-1,3,5-triazine which is a starting material of the instant invention's process.

Melamine (triamino-1,3,5-triazine) and ethanolamine in a 1:2 molar ratio were reacted in the presence of 0.35 mole/kg of reactants of concentrated sulfuric acid as a catalyst at a temperature of between 170° and 180° C. to produce 2,4-dihydroxyethyl-1,3,5-triazine, referred to as hydroxyethylmelamine below.

EXAMPLE 2

In this example, an oxyalkylated polyamino-1,3,5-triazine is prepared.

321 g. (1.5 moles) of the hydroxyethyl melamine (HEM) product of Example 1 was placed in a flask equipped with a reflux condenser and agitating means and it melted at between 105° and 110° C. 12 g. of powdered dry potassium hydroxide was added. The temperature was then raised to 120° C. and $N_2$ was blown over the reaction mixture to remove any moisture.

The temperature was then raised to 130° C. and the addition of propylene oxide (PO) was commenced at a rate of 0.5 ml/min. As the temperature continued to rise to 155° C., the feed rate of PO was increased to 2.5 ml/min. This was accomplished within 6 hours, a moderate reflux being maintained throughout.

Following the addition of 500 g. of propylene oxide (total PO consumption actually amounting to 422 g. (7.3 mole) as measured by the weight increase of the reaction mixture, the temperature was maintained at 155° C. for 20 minutes.

The reaction mixture was then cooled to 100° C. and the potassium hydroxide catalyst was neutralized by the addition of 25 g. of 86% phosphoric acid. Upon further cooling to 60° C., the mixture was diluted with 700 ml of acetone.

After removal of some precipitated salt by filtration, and acetone by vacuum or a steam bath, a high viscous, light amber product is obtained, having the following elemental analysis:

C—51.3%, H—8.4%, and N—15.1%.

EXAMPLE 3

Melamine and ethanolamine were reacted in a 1:3 ratio, respectively, according to the procedure of Example 1 to produce 2,4,6-trihydroxyethyl-1,3,5-triazine.

645 g. (2.5 mole) of the resultant product was then reacted with 1283 g. (20.4 mole) of propylene oxide in the presence of 30 g. of potassium hydroxide according to the procedure outlined in Example 2. The reaction was completed in 10 hours.

The recovered oxypropylated product was light amber in color, having the following elemental analysis:

C—54.28%, H—9.01%, and N—9.21%.

EXAMPLE 4

The procedure of Example 2 is repeated in a pressurized reactor. The hydroxyethyl melamine is replaced by hydroxyisopropyl melamine and the propylene oxide is replaced by ethylene oxide. The ethylene oxide was fed portion-wise as the pressure drop indicated.

An oxyethylated product which is highly viscous and light amber in color is obtained.

What is claimed is:

1. A process for preparing oxyalkylated polyamino-1,3,5-triazines which comprises reacting a hydroxyalkyl ($C_2$–$C_{12}$) or hydroxyaryl polyamino-1,3,5-triazine compound with an alkylene oxide at a temperature between about 80° C. and 200° C. in the substantial absence of a solvent.

2. The process of claim 1 wherein the reaction is conducted at a temperature between about 100° C. and 150° C.

3. The process of claim 1 wherein additionally there is present a basic catalyst in an amount sufficient to catalyze the reaction.

4. The process of claim 3 wherein the basic catalyst is present in an amount equal to from about 0.1 to 1.0 moles per kilogram of hydroxyalkyl or hydroxyaryl polyamino-1,2,5-triazine.

5. The process of claim 3 wherein the basic catalyst is present in an amount equal to from about 0.2 to 0.4 moles per kilogram of hydroxyalkyl or hydroxyaryl polyamino-1,3,5-triazine.

6. The process of claim 3 wherein the basic catalyst is an alkali hydroxide, or an alkali alkoxide with from 1 to 4 carbon atoms.

7. The process of claim 1 wherein the molar ratio of the hydroxyalkyl or hydroxyaryl polyamino-1,3,5-triazine to the alkylene oxide is from about 1:2 to 1:125.

8. The process of claim 1 wherein the mole ratio of the hydroxyalkyl or hydroxyaryl polyamino-1,3,5-triazine to the alkylene oxide is from about 1:4 to 1:40.

9. The process of claim 1 wherein the mole ratio of the hydroxyalkyl or hydroxyaryl polyamino-1,3,5-triazine to the alkylene oxide is from about 1:4 to 1:10.

10. The process of claim 1 or claim 3 wherein the hydroxyalkyl or hydroxyaryl polyamino-1,3,5-triazine has the formula:

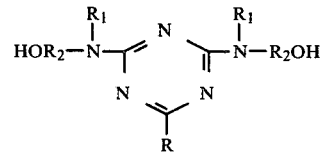

wherein R is selected from the group consisting of hydrogen, alkyl or cycloalkyl with from about 1 to 12 carbon atoms, aryl with from about 6 to 12 carbon atoms, $NH_2$, and $NR_1 R_2 OH$; $R_1$ is selected from the group consisting of hydrogen and $R_2OH$; and each $R_2$ is independently selected from the group consisting of alkylene with from about 2 to 12 carbon atoms and arylene with from about 6 to 12 carbon atoms.

11. The process of claim 10 wherein the alkylene oxide is an unsubstituted alkylene oxide having from about 2 to 6 carbon atoms.

12. The process of claim 10 wherein the hydroxyalkyl polyamino-1,3,5-triazine is di(hydroxyisopropyl)melamine and the alkylene oxide is propylene oxide.

13. The process of claim 10 wherein the hydroxyalkyl polyamino-1,3,5-triazine is di(hydroxyisopropyl)melamine and the alkylene oxide is ethylene oxide.

* * * * *